United States Patent
Mori et al.

(10) Patent No.: US 12,326,388 B2
(45) Date of Patent: Jun. 10, 2025

(54) ABNORMALITY DETECTING DEVICE

(71) Applicant: Nabtesco Corporation, Tokyo (JP)

(72) Inventors: Hiroki Mori, Tokyo (JP); Koji Nakamura, Tokyo (JP); Kazuhiko Sakurai, Tokyo (JP); Masaki Harada, Tokyo (JP)

(73) Assignee: NABTESCO CORPORATION, Tokyo (JP)

( * ) Notice: Subject to any disclaimer, the term of this patent is extended or adjusted under 35 U.S.C. 154(b) by 196 days.

(21) Appl. No.: 18/346,614

(22) Filed: Jul. 3, 2023

(65) Prior Publication Data

US 2024/0011887 A1    Jan. 11, 2024

(30) Foreign Application Priority Data

Jul. 6, 2022   (JP) ................................ 2022-108740
Feb. 22, 2023  (JP) ................................ 2023-026351

(51) Int. Cl.
  *G01N 15/06*   (2024.01)
  *G01N 15/00*   (2024.01)

(52) U.S. Cl.
  CPC . *G01N 15/0656* (2013.01); *G01N 2015/0053* (2013.01)

(58) Field of Classification Search
  CPC ........... G01N 15/0606; G01N 15/0656; G01N 2015/0053; G01N 33/2858
  See application file for complete search history.

(56) References Cited

U.S. PATENT DOCUMENTS

| | | | |
|---|---|---|---|
| 2020/0088350 A1* | 3/2020 | Basso | ..................... B03C 1/286 |
| 2020/0340936 A1 | 10/2020 | Sakurai et al. | |
| 2021/0132126 A1 | 5/2021 | Harada et al. | |
| 2022/0390429 A1 | 12/2022 | Cosoleto et al. | |

FOREIGN PATENT DOCUMENTS

| | | |
|---|---|---|
| EP | 0893683 B1 | 12/2005 |
| FR | 3092010 A1 | 7/2020 |
| JP | 2005-331324 A | 12/2005 |
| JP | 2006-300608 A | 11/2006 |

OTHER PUBLICATIONS

Extended European Search Report dated Nov. 8, 2023, issued in corresponding European Patent Application No. 23183295.7 (7 pgs.).

* cited by examiner

*Primary Examiner* — Judy Nguyen
*Assistant Examiner* — Adam S Clarke
(74) *Attorney, Agent, or Firm* — Pillsbury Winthrop Shaw Pittman, LLP

(57) ABSTRACT

An abnormality detecting device relating to the present disclosure includes at least two first cover parts arranged next to each other in a circumferential direction; a plurality of electrode parts respectively supported by the first cover parts; a plurality of magnet parts provided inside of the first cover parts in the radial direction, where each magnet part is in contact with a corresponding one of the electrode parts; and at least two second cover parts provided between adjacent ones of the first cover parts in the circumferential direction. Each electrode part has an oil-repellent surface.

5 Claims, 5 Drawing Sheets

ABNORMALITY DETECTING DEVICE

CROSS-REFERENCE TO RELATED APPLICATIONS

This application is based on and claims the benefit of priority from Japanese Patent Applications Serial Nos. 2022-108740 (filed on Jul. 6, 2022) and 2023-026351 (Feb. 22, 2023), the contents of which are hereby incorporated by reference in their entirety.

TECHNICAL FIELD

The present disclosure relates to an abnormality detecting device.

BACKGROUND

For example, speed reducers and other mechanical mechanisms are contained in mechanical devices, where the casing of the mechanical devices is filled with lubricant in order to prevent the mechanical mechanisms from wearing out. As such mechanical devices are used over a certain period of time, their mechanical parts may wear off or get damaged. If such occurs, metal powder particles may mix into the lubricant (hereinafter, the metal powder particles in the lubricant will be referred to simply as the metal powder particles). This may compromise the ability of the lubricant to save the mechanisms from being abraded. To address this issue, various abnormality detecting devices have been proposed to detect if the amount of metal powder particles reaches or exceeds a predetermined level.

For example, an abnormality detecting device is disclosed that includes a rod member formed of a conductive material, a holder member holding the rod member, a magnet part provided on the outer periphery of an end of the rod member, a first cover part (an insulating cover) covering the outer periphery of the magnet part, a first electrode part attached to the outer periphery of the first cover part while being in conduction with the rod member, and a second electrode part attached to the outer periphery of the first cover part while being in conduction with the rod member (See Patent Literature 1: Japanese Patent Application Publication No. 2005-331324). The first and second electrode pats are spaced away from each other in the axial direction. The magnet part is configured to magnetically attract metal powder particles, so that the metal powder particles adhere to the electrode parts. The adhering metal powder particles may cause a short circuit between the first and second electrode parts. This can result in detecting that the amount of metal powder particles reaches or exceeds a predetermined level.

The conventional technology described above is effective when oil is used as the lubricant. Contamination of the oil caused by metal powder particles can be checked real time. When grease, which has a higher viscosity than oil, is used, however, the new and highly viscous grease may adhere to the electrode parts. Here, the new grease does not contain a large amount of metal powder particles. The grease may deteriorate as metal powder particles mix, and experience a drop in viscosity. The deteriorated grease having the lowered viscosity can not reach the electrode parts. This may undermine the abnormality detection based on the real-time contamination observation.

SUMMARY

An object of the present disclosure is to provide an abnormality detecting device that is capable of detecting abnormalities real time even when grease, which has a higher viscosity than oil, is used as the lubricant.

(1) An aspect of the present disclosure provides an abnormality detecting device including at least two first cover parts arranged next to each other in a circumferential direction; a plurality of electrode parts respectively supported by the first cover parts, each electrode part having a portion being externally exposed beyond a surface of a corresponding one of the first cover parts; a plurality of magnet parts provided inside of the first cover parts in a radial direction, each magnet part being in contact with a corresponding one of the electrode parts; and at least two second cover parts each provided between adjacent ones of the first cover parts in the circumferential direction. At least a portion of a surface of the each electrode part that is externally exposed beyond a surface of the corresponding first cover part is oil repellent.

The above-described abnormality detecting device may be used in, for example, a speed reducer. When highly viscous grease is used in the speed reducer, the grease can be easily removed from the electrode parts during the initial phase of the lifetime of the speed reducer. According to the above-described invention, the highly viscous grease can be prevented from adhering to the electrode parts. The speed reducer may deteriorate over time and start malfunctioning or breaking down, but, when such happens, no highly viscous grease will be found on the electrode parts. The grease may also deteriorate over time and experience a drop in viscosity. The deteriorated and less viscous grease often contain metal powder particles, which result from the deterioration of the speed reducer over the time. According to the present disclosure, the deteriorated and less viscous grease can directly touch the electrode parts of the abnormality detecting device, which has been continuously used. Accordingly, the above-described abnormality detecting device is capable of detecting abnormalities real time even when grease is used.

(2) The first and second cover parts may each have an oil-repellent surface.

(3) The first and second cover parts may be made of an oil-repellent resin. The electrode parts may have an oil-repellent and conductive plating layer formed on a surface thereof.

(4) The abnormality detecting device may include a first case having the first cover parts, the first case forming an outer shell; and a second case having the second cover parts, the second case forming the outer shell. The first and second cases may be made of the oil-repellent resin.

(5) Another aspect of the present disclosure provides an abnormality detecting device including a first case having at least two first cover parts arranged next to each other in a circumferential direction, the first case forming an outer shell; a plurality of electrode parts respectively supported by the first cover parts, each electrode part having a portion externally exposed beyond a surface of a corresponding one of the first cover parts; a plurality of magnet parts provided inside of the first cover parts in a radial direction, each of the magnet parts being in contact with a corresponding one of the electrode parts; a second case having at least two second cover parts, each second cover part being provided between adjacent ones of the first cover parts in the circumferential direction, the second case forming the outer shell; and a detecting unit for detecting a resistance between two of the electrode parts via the magnet parts to determine whether an abnormality occurs based on the detected resistance. At least a portion of a surface of the each electrode part that is externally exposed beyond a surface of the corresponding first cover part has an oil-repellent and conductive plating layer formed thereon. The first and second cases are made of an oil-repellent resin.

The above-described abnormality detecting device may be used in, for example, a speed reducer. When highly viscous grease is used in the speed reducer, the grease can be easily removed from the electrode parts during the initial phase of the lifetime of the speed reducer. According to the above-described invention, the highly viscous grease can be prevented from adhering to the first and second cover parts. In this manner, a spacious oil-repellent region can be provided so as to surround the electrode parts of the abnormality detecting device. An oil-repellent material may be sprayed or applied in other manners later. In this case, the oil-repellent material may be applied unevenly. The present disclosure, however, can avoid such drawbacks. The highly viscous grease can be thus prevented from adhering to the electrode parts and cases. The speed reducer may deteriorate over time and start malfunctioning or breaking down, but, when such happens, no highly viscous grease will be found on the electrode parts or cases. The grease may also deteriorate over time and experience a drop in viscosity. The deteriorated and less viscous grease often contains metal powder particles, which result from the deterioration of the speed reducer over the time. According to the present disclosure, the deteriorated and less viscous grease can directly touch the electrode parts of the abnormality detecting device, which has been continuously used. Accordingly, the above-described abnormality detecting device is capable of detecting abnormalities real time even when grease is used.

The abnormality detecting device relating to the present disclosure is capable of detecting abnormalities real time even when grease, which has a higher viscosity than oil, is used as the lubricant.

DESCRIPTION OF THE PREFERRED EMBODIMENTS

The embodiments of the present disclosure will be hereinafter described with reference to the drawings.

Speed Reducer

Figure 1:
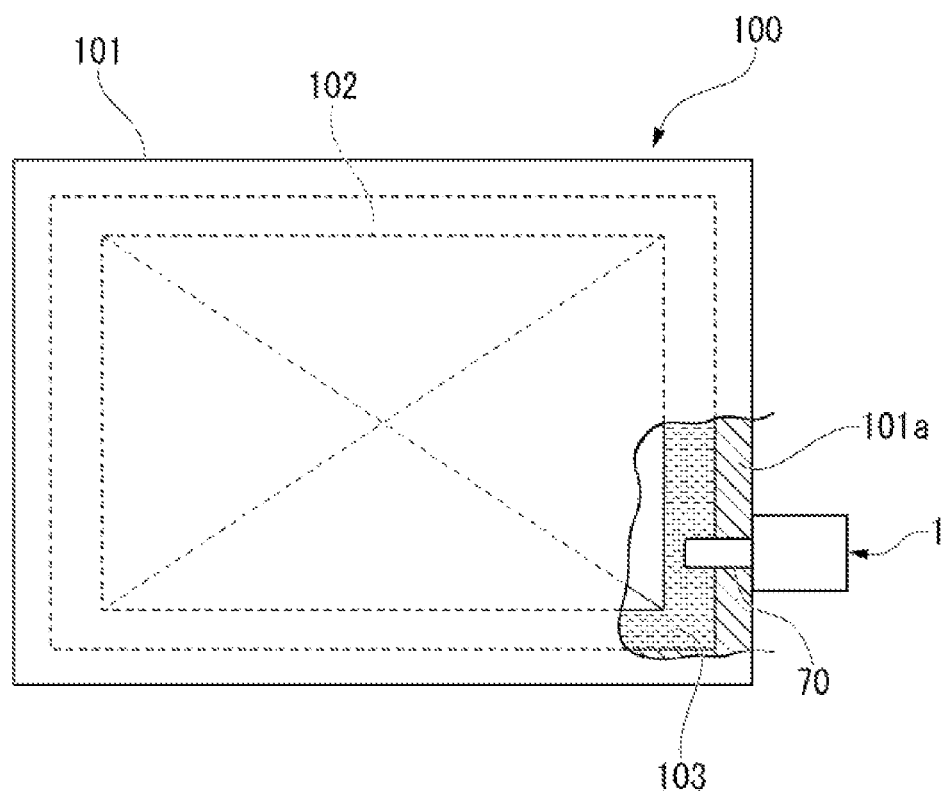
FIG. 1 schematically shows the configuration of a speed reducer relating to an embodiment of the present disclosure.

FIG. 1 schematically shows an example of a speed reducer 100 having an abnormality detecting device 1 relating to the present disclosure provided therein. The speed reducer 100 shown in FIG. 1 is an example of a mechanical device. The speed reducer 100 is used in, for example, the joints of industrial robots used in the production lines of plants. As shown in FIG. 1, the speed reducer 100 includes a casing 101 and a speed reducing mechanism 102 housed in the casing 101. The speed reducing mechanism 102 reduces the speed of the rotation input from a power source, which is not shown, at a predetermined reduction ratio.

The casing 101 is filled with a non-conductive lubricant 103. The speed reducing mechanism 102 is immersed in the lubricant 103. In other words, the speed reducing mechanism 102 employs grease or oil bath lubrication.

The following describes in detail a case where grease lubrication is employed. When grease fills the casing 101, the flowability inside the casing 101 is lower than when oil bath is employed due to the nature of the grease. The grease exhibits a high viscosity immediately after filling the casing 101. The grease, however, progressively deteriorates as the speed reducer 100 is driven and the grease is thus agitated. This resultantly lowers the viscosity of the grease.

Therefore, when grease is used as the lubricant 103 to fill the internal space within the casing 101, the grease is aggressively agitated so that the grease may deteriorate and partly experience a drop in viscosity. Part of the grease, however, is not agitated very much, and another part of the grease may keep the initial viscosity, which is exhibited immediately after the grease fill the casing 101. This means that the lubricant 103 also has a part of high viscosity. The lubricant 103 thus has a low-viscosity part and a high-viscosity part. The highly viscous part of the lubricant 103 is likely to adhere to the speed reducer 100 and the abnormality detecting device 1. The low-viscosity part of the lubricant 103, on the other hand, has a large amount of conductive particles such as metal powder particles (for example, metal powder particles (initial abrasion powder particles and over-time metal powder particles described below).

Abnormality Detecting Device

Figure 2:
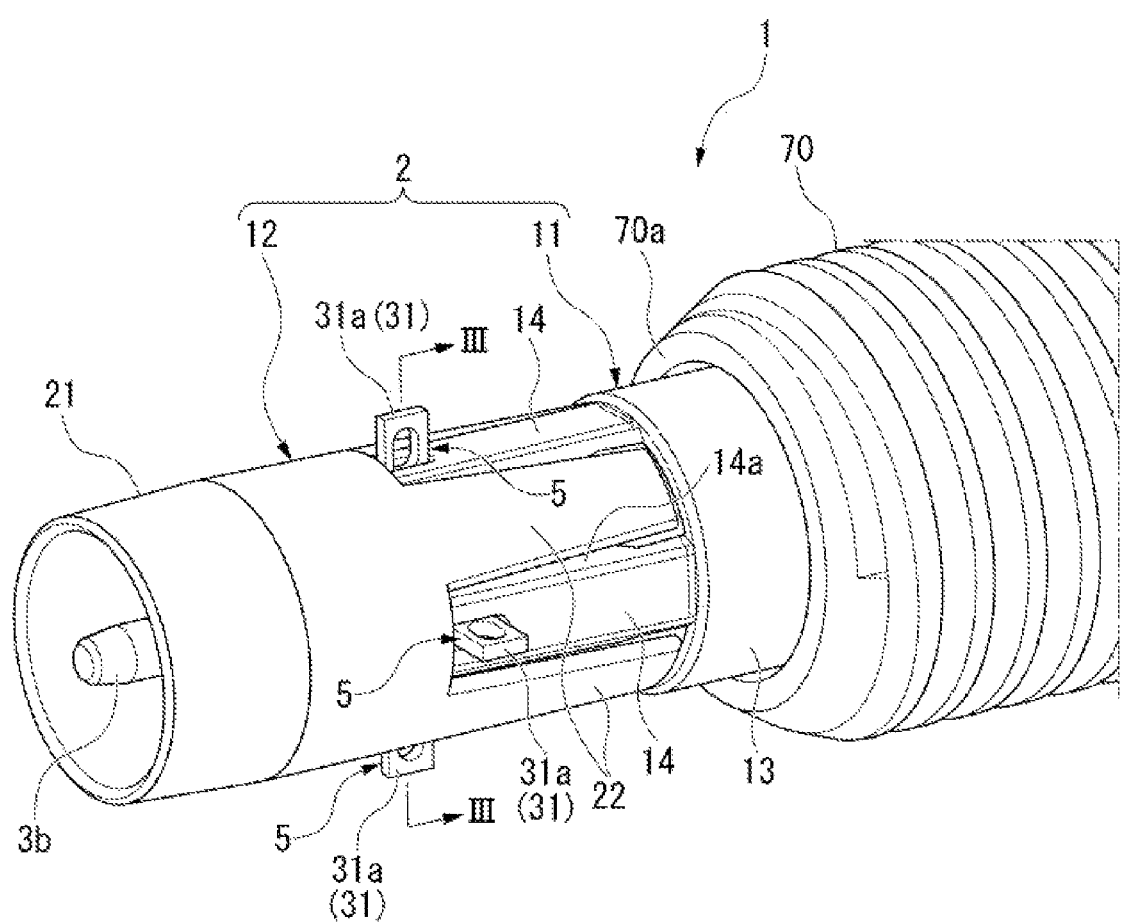
FIG. 2 is a perspective view showing the abnormality detecting device relating to the embodiment of the present disclosure.
Figure 3:
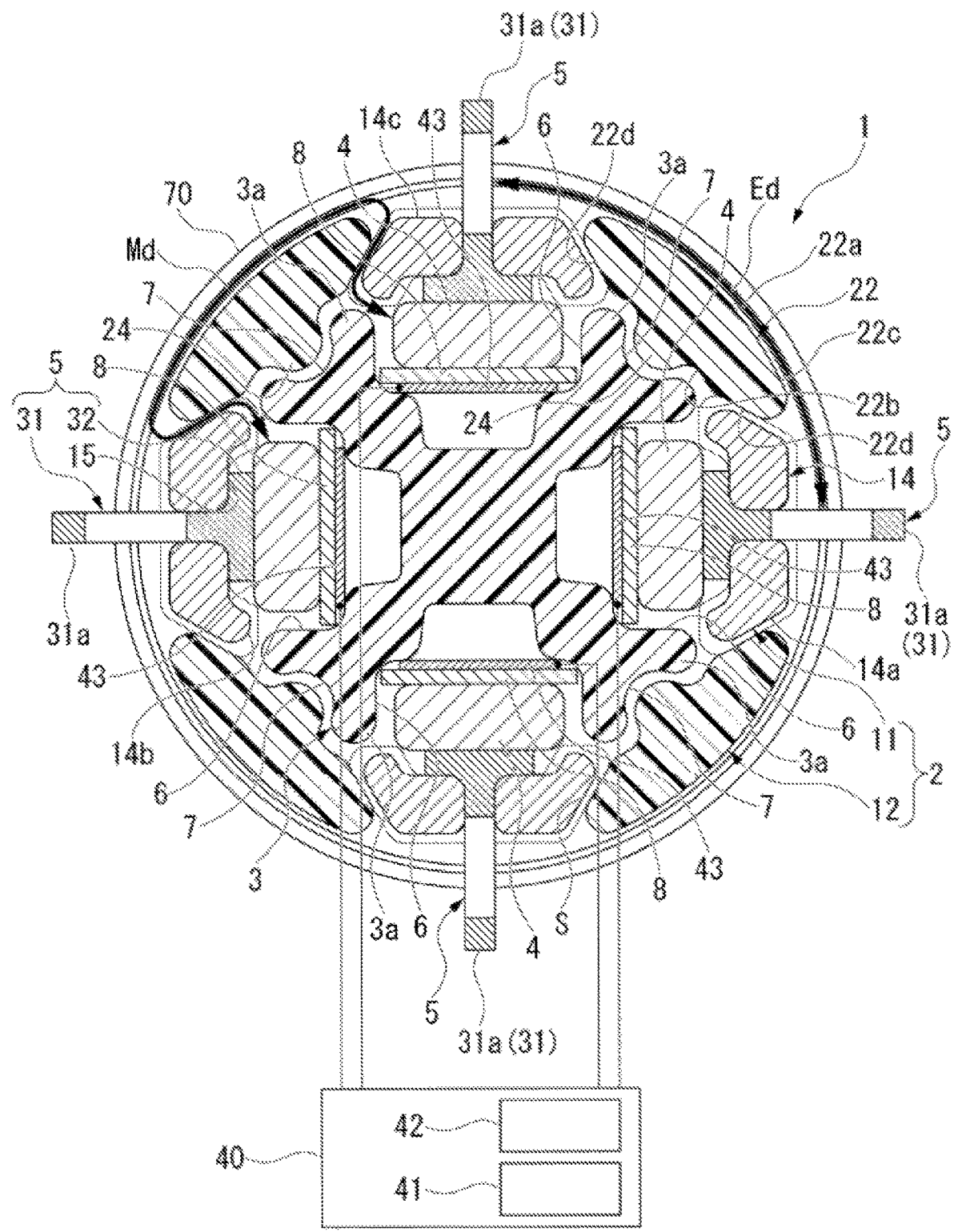
FIG. 3 is a sectional view along the line in FIG. 2.
Figure 4:
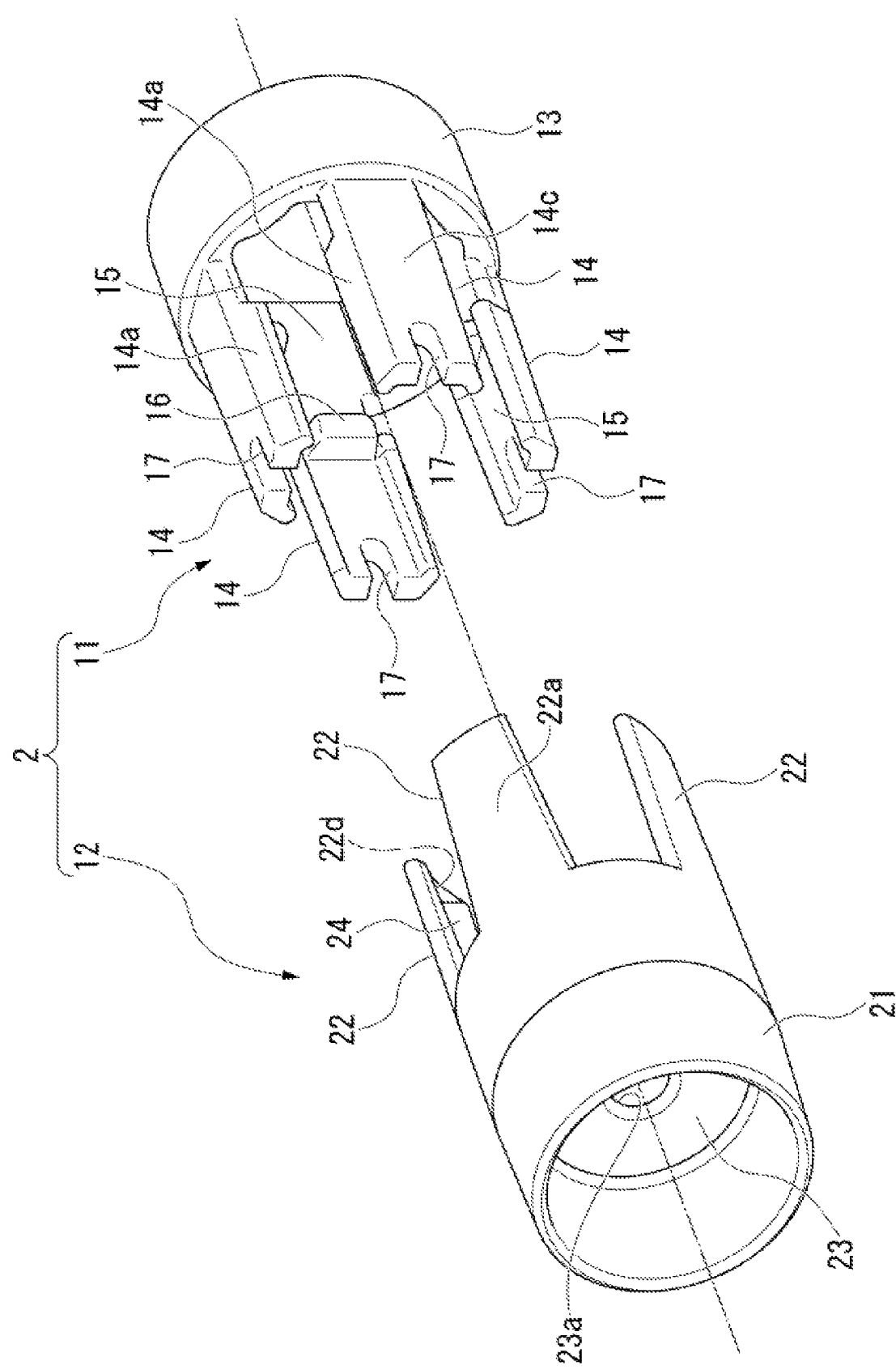
FIG. 4 is an exploded perspective view showing a casing relating to the embodiment of the present disclosure.

FIG. 2 is a perspective view of the abnormality detecting device 1. FIG. 3 is a sectional view along the line III-III in FIG. 2. FIG. 4 is an exploded perspective view showing a casing 2 constituting the abnormality detecting device 1. As shown in FIGS. 2 to 4, the abnormality detecting device 1 includes an externally threaded part 70 attached to the wall 101a of the casing 101, a support 3 shaped like a rectangular rod and inserted into the externally threaded part 70, four magnet parts 4 supported on the support 3, the tubular casing 2 surrounding and covering the support 3 and magnet parts 4, and four electrode parts 5 provided on the casing 2.

The wall 101a of the casing 101 has an internally threaded part, which is not shown. The externally threaded part 70 is tightened into the internally threaded part. In this manner, the abnormality detecting device 1 can be mounted to the wall 101a of the casing 101. The externally threaded part 70 has a seal flange part (not shown) integrally formed therewith, which is positioned on the outside (on the right side in FIG. 2) of the wall 101a. The seal flange part abuts the wall 101a, which reliably seals the wall 101a of the casing 101 and the abnormality detecting device 1. In the following description, the terms "axial direction," "axially" and "axial" refer to the axial direction of the externally threaded part 70. Similarly, the terms "circumferential direction," "circumferentially" and "circumferential" refer to the circumferential direction of the externally threaded part 70. The terms "radial direction," "radially" and "radial" refer to the radial direction of the externally threaded part 70, which is orthogonal to the axial and circumferential directions.

A through-hole, which is not shown, extends through the externally threaded part 70 in the axial direction. The support 3 is received in the through hole. The support 3 is made of, for example, a resin. The central axis of the externally threaded part 70 is aligned with the central axis of the support 3. The end of the support 3 (the left end in FIG. 2) protrudes beyond an end 70a of the externally threaded part 70 toward and into the casing 101. The protruding part of the support 3 beyond the end 70a of the externally threaded part 70 has four surfaces, which respectively have magnet housing depressions 6.

The four magnet housing depressions 6 are long in the axial direction and arranged at even intervals in the circumferential direction. Between every adjacent two of the magnet housing depressions 6 in the circumferential direction of the support 3, in other words, corners 3a of the support 3 that are adjacent to each other in the circumferential direction respectively have case receiving depressions 7. The case receiving depressions 7 receive ridges 24 of the casing 2, which will be described below.

In each of the magnet housing depressions 6, a plate-shaped relay piece 8 is provided. The relay pieces 8 are formed of a metal magnetic material. The magnet parts 4 are provided on the relay pieces 8. The magnet parts 4 are shaped like a bar long in the axial direction, which correspond to the shape of the magnet housing depressions 6. The magnet parts 4 are conductive magnets and exhibit magnetic properties without magnetic field or current applied thereto from outside. The magnet parts 4 are fixedly attached to the relay pieces 8 through magnetic force.

The casing 2 is made of, for example, a resin. The casing 2 is cylindrically shaped so as to surround and cover the magnet parts 4 and support 3 protruding beyond the externally threaded part 70. The casing 2 is configured such that it can be divided into a first case 11 and a second case 12, which are arranged next to each other in the axial direction. The first case 11 is positioned closer to the externally threaded part 70. The first case 11 has an oil-repellent surface. The first case 11 has a first cylindrical part 13 and four first cover parts 14. The first cylindrical part 13 is designed to abut against the end 70a of the externally threaded part 70, and the first cover parts 14 extend in the axial direction from the first cylindrical part 13 toward the second case 12.

The four first cover parts 14 are arranged at equal intervals in the circumferential direction. The four first cover parts 14 have an oil-repellent surface. The four first cover parts 14 are located radially outside the magnet parts 4 while the first case 11 is mounted onto the support 3. The first cover parts 14 are shaped like a plate and arranged such that their thickness direction is aligned with the radial direction. The first cover parts 14 are elastically deformable in the radial direction, so that the first cover parts 14 slightly elastically presses the magnet parts 4 from radially outside. The side surfaces 14a of the first cover parts 14 facing the circumferential direction (the circumferential ends) are sloped such that the width of the first cover parts 14 in the circumferential direction is smaller on the outer side in the radial direction than on the inner side. A recess 15 is formed in the inner peripheral surface 14b of each first cover part 14 along its entire length in the axial direction and a large part of it in the circumferential direction.

A restraining projection 16 is formed in the recess 15 in each first cover part 14. The restraining projection 16 is positioned in the recess 15 at the center in the axial direction. The restraining projection 16 extends along the entire length of the recess 15 in the circumferential direction. The restraining projection 16 is positioned on the end of the magnet part 4 that faces the externally threaded part 70 while the first case 11 is attached to the support 3. In this manner, the restraining projections 16 can restrain the movement of the magnet parts 4 in the axial direction. The end of each first cover part 14 that faces the second case 12 has a retaining groove 17 formed therein. The retaining groove 17 is positioned in the first cover part 14 at the center in the circumferential direction. The retaining groove 17 of each first cover part 14 receives and retains the corresponding one of the electrode parts 5. The electrode parts 5 will be described below in detail.

The second case 12 has an oil-repellent surface. The second case 12 has a second cylindrical part 21 and four second cover parts 22. The second cover parts 22 extend in the axial direction from the second cylindrical part 21 toward the first case 11. A sealing plate 23 is integrally formed with the second cylindrical part 21 at the center in the axial direction. A through hole 23a is formed in the sealing plate 23 at the center in the radial direction and extends through the sealing plate 23 in the thickness direction. The through hole 23a receives therein a support shaft 3b (see FIG. 2), which is integrally formed with the support 3 at its end. This results in the second case 12 supporting the end of the support 3.

The four second cover parts 22 are arranged at equal intervals in the circumferential direction. The four second cover parts 22 have an oil-repellent surface. The four second cover parts 22 are located to fill the spaces between adjacent ones of the first cover parts 14 in the circumferential direction while the second case 12 is mounted onto the support 3. The second cover parts 22 are shaped like a plate and arranged such that their thickness direction is aligned with the radial direction. More specifically, the second cover parts 22 each have an outer peripheral surface 22a and an inner peripheral surface 22b formed in the shape of an arc around the central axis of the support 3, and also have side surfaces 22c (circumferential ends) connecting the outer and inner peripheral surfaces 22a and 22b.

To make the surface of the casing 2 oil-repellent, an oil-repellent coating agent may be sprayed or applied using a brush to the surface of the casing 2. Alternatively, the casing 2 may be made of an oil-repellent resin. Such a resin includes a fluororesin and the like. When made of an oil-repellent material, the casing 2 can be more uniformly oil-repellent than when the casing 2 has an oil repellent coating agent applied thereon. This is because the coating agent may be unevenly applied.

Stated differently, to make the surface of the first and second cases 11 and 12 oil-repellent, an oil-repellent coating agent may be sprayed or applied using a brush to the surface of the first and second cases 11 and 12. Alternatively, the first and second casings 11 and 12 may be made of an oil-repellent resin. Such a resin includes a fluororesin and the like. When made of an oil-repellent material, the first and second cases 11 and 12 can be more uniformly oil-repellent than when the first and second casings 11 and 12 have an oil repellent coating agent applied thereon. This is because the coating agent may be unevenly applied.

It is not necessary to make the entire surface of the first and second cases 11 and 12 oil repellent. It is acceptable as long as at least the surfaces surrounding the electrode parts 5 are oil repellent. Specifically, what is least required is that the first and second cover parts 14 and 22 have an oil-repellent surface.

The side surfaces 22c face the circumferential direction and are curved such that they are swollen outwardly from the outer and inner peripheral surfaces 22a and 22b in the circumferential direction. The side surfaces 22c are located outside the side surfaces 14a of the first cover parts 14 in the radial direction while the second case 12 is attached to the support 3. Stated differently, when seen in the radial direction, the side surfaces 14a of the first cover parts 14 overlap the side surfaces 22c of the second cover parts 22. The side surfaces 22c of the second cover parts 22 each have a slope part 22d that is positioned close to the inner peripheral surface 22b. In compliance with the shape of the side surfaces 14a of the first cover parts 14, the slope parts 22d are sloped such that the width of the second cover parts 22 in the circumferential direction is larger on the outer side in the radial direction than on the inner side. The slope parts 22d are overlaid on the side surfaces 14a of the first cover parts 14. The second cover parts 22 hold the first cover parts 14 of the first case 11 down from the outside in the radial direction.

The ridge 24 is formed on the inner peripheral surface 22b of each second cover part 22. The ridge 24 is positioned on the inner peripheral surface 22b at the center in the circumferential direction and extends in the axial direction. The ridges 24 are housed in the case receiving depressions 7 in the support 3. In this way, the second case 12 can be rightly positioned relative to the support 3 in the circumferential direction. Via the second case 12, the first case 11 can be also rightly positioned relative to the support 3.

The electrode parts 5, which are retained in the retaining grooves 17 in the first cover parts 14 of the first case 11, are made of a non-magnetic conductive material such as brass, aluminum and copper. The electrode parts 5 have an oil-repellent surface. When cut along the radial and circumferential directions, the electrode parts 5 have a T-shaped section. When seen in the section along the radial and circumferential directions, the electrode parts 5 each have an electrode body 31 and a magnet abutting plate 32. The electrode body 31 extends along the radial direction, and the magnet abutting plate 32 is integrated with the radially inner end of the electrode body 31 and extends in the circumferential direction when seen in the section along the radial and circumferential directions.

To make the surface of the electrode parts 5 oil-repellent, an oil-repellent coating agent may be sprayed or applied using a brush to the surface of the electrode parts 5. Alternatively, the electrode parts 5 may be subjected to surface treatment, so that an oil-repellent and conductive plating layer may be formed. The plating layer may be, for example, an electroless nickel plating containing a fluororesin. When the electrode parts 5 undergo surface treatment, the electrode parts 5 can be more uniformly oil-repellent than when the electrode parts 5 have an oil repellent coating agent applied thereon. This is because the coating agent may be unevenly applied.

The retaining grooves 17 in the first case 11 receive the electrode bodies 31. This allows the electrode bodies 31 to be in communication with the inside and outside of the first cover parts 14 in the radial direction. Accordingly, the radially inner and outer ends of the electrode bodies 31 protrude out of the first cover parts 14. The magnet abutting plates 32 are housed in the recesses 15 in the first cover parts 14. The magnet abutting plates 32 can prevent the electrode parts 5 from moving outward in the radial direction. Here, the surface of the electrode parts 5 represents a part of the entire surface of the electrode parts 5 that protrudes at least beyond the first cover parts 14 (protruding part). It is acceptable as long as at least the protruding part is oil repellent. The present embodiment, however, is not limited to such. For example, in addition to the surface of the electrode parts 5, a part of the entire surface of the electrode parts 5 that is inside the first cover parts 14 may be also oil repellent.

The first cover parts 14 slightly elastically press the magnet parts 4 from the outside in the radial direction. This means that the magnet abutting plates 32 are elastically pressed by the first cover parts 14 against the magnet parts 4. In this way, a sufficient contact can be established between the magnet parts 4 and the magnet abutting plates 32, so that electrical communication can be achieved between the electrode parts 5 and the magnet parts 4. Since the electrode parts 5 are non-magnetic, they are electrically connected to the magnet parts 4 without being magnetized. The first cover parts 14, which hold the electrode parts 5 down, are arranged such that their side surfaces 14a are overlaid on the side surfaces 22c of the second cover parts 22 in the radial direction. The first cover parts 14 are thus held down by the second cover parts 22 from the outside in the radial direction. In this way, the first cover parts 14 can reliably keep the electrode parts 5 holding down the magnet parts 4.

Since the side surfaces 14a of the first cover parts 14 are overlaid on the side surfaces 22c of the second cover parts 22 in the radial direction, the micro-gap S between the first and second cover parts 14 and 22 has a complicated shape. In other words, the micro-gap S between the first cover parts 14 and the second cover parts 22 has such a bent shape that, as it extends in the radial direction from the outer side toward the inner side, it extends along the side surfaces 22c of the second cover parts 22 in the circumferential direction from the outer side toward the inner side. Accordingly, the creepage distance Ed between adjacent ones of the electrode parts 5 (electrode bodies 31) in the circumferential direction (hereinafter referred to as the inter-electrode creepage distance Ed) is less than the creepage distance Md between adjacent ones of the magnet parts 4 in the circumferential direction (hereinafter referred to as the inter-magnet creepage distance Md), where the inter-electrode creepage distance Ed is directed along the outer peripheral surfaces 14c of the first cover parts 14 and along the outer peripheral surface 22a of the second cover part 22, and the inter-magnet creepage distance Md is directed along the respective sides (side surfaces 22c) of the second cover part 22 in the circumferential direction and along the outer peripheral surface 22a of the second cover part 22.

Here, the term "creepage distance" denotes the minimum distance between two members along the surface of an insulating material. In the present embodiment, specifically, the creepage distance denotes the minimum distance between adjacent ones of the electrode parts 5 (target members) in the circumferential direction and between adjacent ones of the magnet parts 4 (target members) in the circumferential direction along the surface of the casing 2 (insulating material). In other words, the creepage distance denotes the shortest distance along the surface of the insulating material between the two target members that need to be insulated from each other. The effects produced by the fact that the inter-electrode creepage distance Ed is less than the inter-magnet creepage distance Md will be described below.

Figure 5:
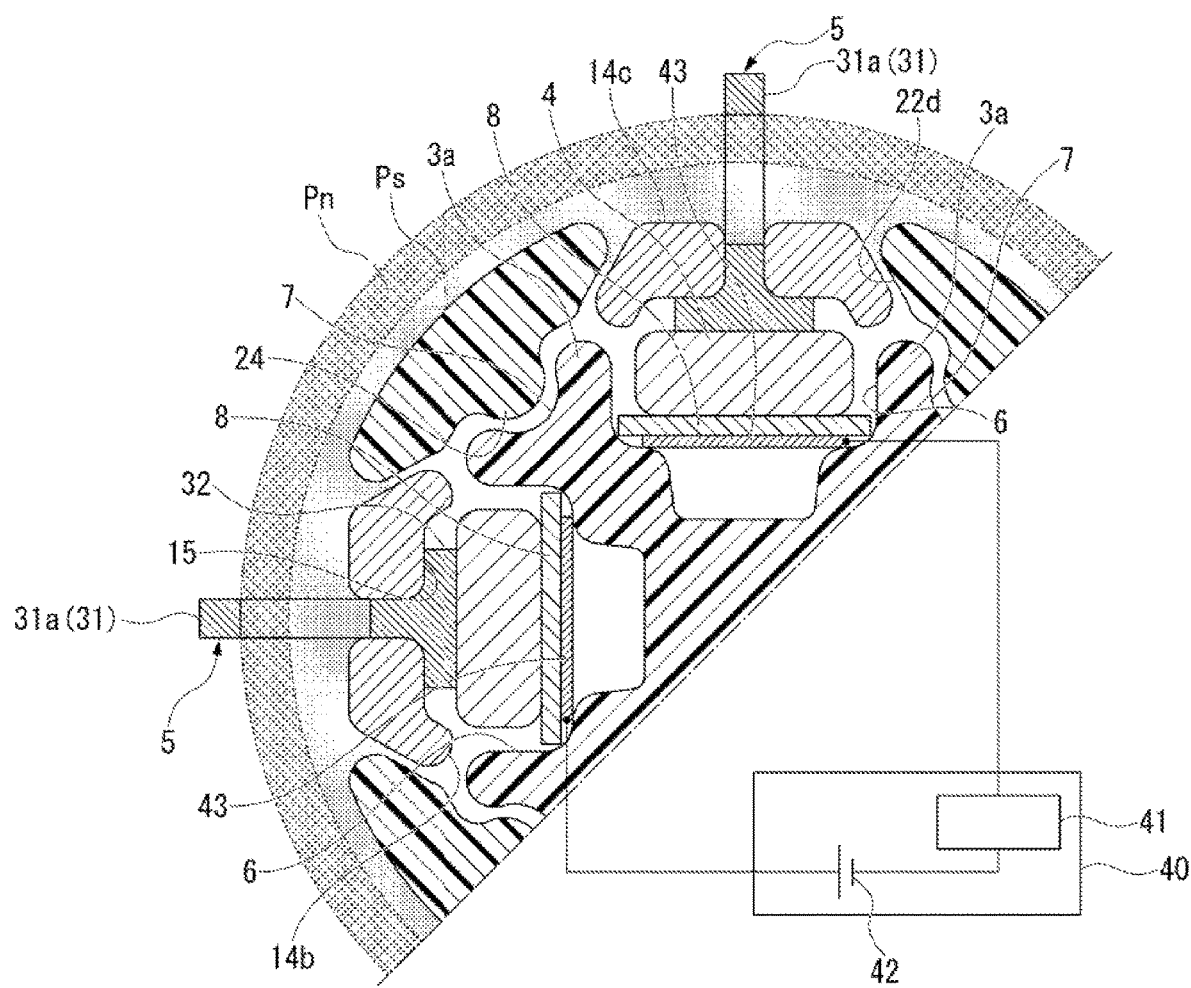
FIG. 5 illustrates an abnormality detecting method employed by the abnormality detecting device relating to the embodiment of the disclosure.

The above-described abnormality detecting device 1 is electrically connected to a detection circuit 40 for detecting abnormalities using the abnormality detecting device 1 (see also FIG. 5). The detection circuit 40 has a circuit board 43, a resistance detecting unit 41 and a power supply 42. The circuit board 43 is connected to the relay pieces 8, and the resistance detecting unit 41 and power supply 42 are connected to the relay pieces 8 via the circuit board 43.

The power supply 42 applies voltage to any one of the electrode parts 5. The resistance detecting unit 41 is configured to detect the resistance between the electrode part 5 to which voltage is applied and an adjacent one of the other electrode parts 5 in the circumferential direction. The detection circuit 40 observes how the detected resistance changes and, based on it, can detect the amount of conductive particles such as metal powder particles in the lubricant 103 in the speed reducer 100. Based on the result, the abnormality detecting device 1 is configured to detect abnormalities of the speed reducer 100. The following specifically describes how the abnormality detecting device 1 detects abnormalities of the speed reducer 100.

How Abnormality Detecting Device Detects Abnormalities of Speed Reducer

The following describes how the abnormality detecting device 1 detects abnormalities of the speed reducer 100 with reference to FIG. 5. FIG. 5 illustrates the abnormality detecting method employed by the abnormality detecting device 1 and shows part of the view in FIG. 3 in an enlarged state. The following first describes initial abrasion powder particles (metal powder particles) having a fine particle size, which is produced when the speed reducer 100 is used for the first time (in other words, during the initial phase of operation). The initial abrasion powder particles are fine metal powder particles with a particle size of, for example, less than 10 µm (usually less than approximately 2 µm) and has little adverse effects on the operation of the speed reducer 100.

As shown in FIG. 1, the casing 2 shown in FIG. 2 protrudes into the casing 101 of the speed reducer 100, so that the casing 2 is immersed in the lubricant 103. As shown in FIG. 5, the initial abrasion powder particles are magnetically attracted by the magnet parts 4 of the abnormality detecting device 1 to adhere to the surface of the casing 2, specifically, to the outer peripheral surfaces 14c of the first cover parts 14 and the outer peripheral surfaces 22a of the second cover parts 22 in the form of a lower layer Ps. The adhering initial abrasion powder particles are surrounded by the lubricant 103, which forms a non-conductive layer. During the initial phase of the lifetime, the resistance detecting unit 41 detects an infinite resistance since the lubricant 103 is non-conductive. In addition, since the initial abrasion powder particles adhere with a relatively weak force, only a small amount of initial abrasion powder particles is deposited between adjacent ones of the electrode parts 5 in the circumferential direction.

Since the electrode parts 5 are made of a non-magnetic conductive material, there is no chance that the electrode parts 5 are magnetized under the influence of the magnetic force produced by the magnet parts 4. This prevents the initial abrasion powder particles from adhering to the protruding parts 31a of the electrode bodies 31 of the electrode parts 5 that protrude outward in the radial direction beyond the first cover parts 14. In this manner, during the initial phase of operation of the speed reducer 100, the protruding parts 31a can avoid being covered with the initial abrasion powder particles. If the protruding parts 31a are buried in the initial abrasion powder particles, the detection circuit 40 is not capable of accurately detecting whether the over-time metal powder particles adhere, which may occur after a certain period of time after the initial abrasion powder particles are generated.

The following now describes the over-time metal powder particles. The over-time metal powder particles include metal powder particles (abrasion powder particles) and broken fragments (metal fragments) that are generated after a certain period of time elapses after the initial abrasion powder particles are generated, in other words, that are generated as the speed reducer 100 is used in an ordinary manner. The over-time metal powder particles have a large particle size, for example, 10 µm or more. Therefore, the over-time metal powder particles are easily affected by the magnetic force produced by the magnetic parts 4. The over-time metal powder particles push away the non-conductive lubricant and attract each other.

As the amount of over-time metal powder particles in the lubricant 103 increases, the over-time metal powder particles are magnetically attracted to the magnet parts 4. The over-time metal powder particles adhere to the outer peripheral surfaces 14c of the first cover parts 14 and the outer peripheral surfaces 22a of the second cover parts 22 between adjacent ones of the electrode parts 5 in the circumferential direction. The over-time metal powder particles are subject to the magnetic force produced by the magnet parts 4 and deposited as an upper layer Pn on top of the lower layer Ps, which adheres to the outer peripheral surfaces 14c of the first cover parts 14 and the outer peripheral surfaces 22a of the second cover parts 22.

When the amount of over-time metal powder particles deposited on the outer peripheral surfaces 14c of the first cover parts 14 and the outer peripheral surfaces 22a of the second cover parts 22 reaches or exceeds a specified amount, the resistance detecting unit 41 detects a resistance equal to or less than a specified value. When the detected resistance reaches or falls below the specified value, the detection circuit 40 determines that the speed reducer 100 experiences abnormalities. In this manner, the abnormality detecting device 1 can detect abnormalities of the speed reducer 100.

In the abnormality detecting device 1, the micro-gap S is left between each first cover part 14 and the corresponding second cover part 22. For example, the broken fragments (metal fragments) or the like may get into the micro-gap S and adhere directly to the magnet parts 4. If such occurs, the broken pieces (metal fragments) may cause a short-circuit between adjacent ones of the magnet parts 4 in the circumferential direction. As shown in FIG. 3, however, the inter-electrode creepage distance Ed is less than the inter-magnet creepage distance Md. This prevents a short circuit from being caused by the metal powder particles or the like between the adjacent magnet parts 4 in the circumferential direction at least until the resistance detected by the resistance detecting unit 41 reaches or falls below the specified value.

Comparative Example

For the comparison purpose, the following describes an example case where grease is used as the lubricant 103, the casing 2 does not have an oil-repellent surface, and the electrode parts 5 do not have an oil repellent surface. The inventors have conducted tests to discover whether the above-described abnormality detecting device 1 could be used to detect abnormalities real time even when the lubricant 103 was grease. More specifically, the casing 101 was filled only with, as the lubricant 103, deteriorated grease, that is to say, grease that had metal powder particles mixed therein and thus exhibited a low viscosity. This means that the speed reduction mechanism 102 of a new speed reducer 100 was immersed in the deteriorated grease, which served as the lubricant 103.

As the electrode parts 5 of the abnormality detecting device 1, electrode parts 5 to which new grease, specifically speaking, grease having a high viscosity and no metal powder particles, was applied (adhered) and electrode parts 5 to which no grease was applied were provided. The tests were conducted such that the speed reducer 100 operated for a predetermined period of time and the abnormality detecting device 1 attempted to detect metal powder particles on the electrode parts 5 (see Table 1).

The results of the tests showed that no metal powder particles were detected on the electrode parts 5 to which the new grease was applied (adhered) even if the deteriorated grease was used as the lubricant 103. On the other hand, metal powder particles were detected on the electrode parts 5 to which no grease was applied. From these findings, the inventors have identified the following problem. The abnormality detecting device 1 is incapable of detecting metal powder particles or the like if grease that has not deteriorated and still has a high viscosity (i.e., the state of the grease immediately after the grease fills the internal space and during the initial phase of the lifetime of the speed reducer 100) adheres to the electrode parts 5 of the abnormality detecting device 1.

TABLE 1

| How Tests Are Conducted | Electrode Parts of Abnormality Detecting Device | Results |
| --- | --- | --- |
| Deteriorated Grease Used As Lubricant 103 Filling Casing 101, Speed Reduction Mechanism 102 of New Speed Reducer 100 Immersed in Deteriorated Grease New Grease Applied to Electrode Parts 5 in Abnormality Detecting Device 1, Nothing Applied to Electrode Parts 5 in Another Abnormality Detecting Device 1 After Speed Reducer 100 is Operated for Predetermined Period of Time, Abnormality Detecting Device 1 are Used to Detect Metal Powder Particles | 1: New Grease Not Adhering to Electrode Parts 5 2: New Grease Adhering to Electrode Parts 5 | Metal Powder Particles Detected After Speed Reducer 100 Operated for Predetermined Period of Time No Metal Powder Particles Detected After Speed Reducer 100 Operated for Predetermined Period of Time |

When the tests were actually conducted, new grease that had a high viscosity and no metal powder mixed therein was applied to the entire casing 2, which constituted the abnormality detecting device 1.

The abnormality detecting device 1 is mounted to the wall 101*a* of the casing 101. The abnormality detecting device 1 is mounted at a site where the lubricant 103 is highly flowable. The abnormality detecting device 1 is configured to detect an abnormality of the speed reducer 100 by detecting the amount of conductive particles such as metal powder particles in the lubricant 103 (for example, metal powder particles described below).

Consequently, the above-described abnormality detecting device 1 can more reliably detect metal powder particles or the like than the device relating to the comparative example. In the abnormality detecting device 1, at least a part of each electrode part 5 that outwardly protrude (is externally exposed) beyond the outer peripheral surface 14*c* of the corresponding first cover part 14 has an oil-repellent surface. This allows the high-viscosity grease (lubricant 103) to be easily removed from the electrode parts 5 during the initial stage of the lifetime of the speed reducer 100. In this manner, the highly viscous grease can be prevented from adhering to the electrode parts 5. The speed reducer 100 may deteriorate over time and start malfunctioning or breaking down. When such occurs, no high-viscosity grease will be found on the electrode parts 5. The grease may also deteriorate over time and experience a drop in viscosity. The deteriorated and less viscous grease often contain metal powder particles, which result from the deterioration of the speed reducer 100 over time. The deteriorate and less viscous grease can directly touch the electrode parts 5 of the abnormality detecting device 1, which has been continuously used. Accordingly, the above-described abnormality detecting device 1 is capable of detecting abnormalities real time even when grease is used.

The first and second cover parts 14 and 22 are made of an oil-repellent resin. The electrode parts 5 have an oil-repellent and conductive plating layer formed on a surface thereof. This prevents the highly viscous grease from adhering to the first and second cover parts 14 and 22, which support the electrode parts 5, so that the abnormalities can be detected more accurately. An oil-repellent material may be sprayed or applied onto the first and second cover parts 14 and 22. In this case, the oil-repellent material may be applied unevenly. The present disclosure, however, can avoid such drawbacks.

In addition to the first and second cover parts 14 and 22, the first and second cases 11 and 12 are also made of an oil-repellent resin. Therefore, a spacious oil-repellent region can be provided so as to surround the electrode parts 5 of the abnormality detecting device 1. It is thus made sure that the highly viscous grease can be easily removed from the electrode parts 5 and prevented from adhering to the electrode parts 5. An oil-repellent material may be sprayed or applied onto the first and second cases 11 and 12. In this case, the oil-repellent material may be applied unevenly. The present disclosure, however, can avoid such drawbacks.

Therefore, the detection circuit 40 can detect that the amount of metal powder particles reaches or exceeds the specified amount, and the abnormality detecting device 1 described in the above can thus accurately determine whether abnormalities occur in the speed reducer 100. In order to allow the inter-electrode creepage distance Ed to be less than the inter-magnet creepage distance Md, the side surfaces 14*a* of the first cover parts 14 are overlaid on the side surfaces 22*c* of the second cover parts 22 in the radial direction. According to the present embodiment, a long inter-magnet creepage distance Md can be achieved simply and easily, so that the inter-electrode creepage distance Ed can be less than the inter-magnet creepage distance Md.

In the abnormality detecting device 1, the four first cover parts 14 are arranged at equal intervals in the circumferential direction, and so are the four second cover parts 22. Corresponding to the electrode parts 5 provided in the first cover parts 14, the four magnet parts 4 are provided at equal intervals in the circumferential direction. With such arrangement, the amount of metal powder particles can be detected anywhere over the entire circumference of the abnormality detecting device 1, which can contribute to further improve the accuracy of detection performed by the abnormality detecting device 1.

In the abnormality detecting device 1, the electrode parts 5 are separate from the magnet parts 4. The first cover parts 14 are elastically deformable in the radial direction, to energize the electrode parts 5 toward the magnet parts 4. The abnormality detecting device 1 can be readily manufactured without requiring complicatedly shaped electrode and magnet parts 5 and 4 while the electrode parts 5 can be reliably in electrical communication with the magnet parts 4.

The embodiments described herein are not intended to necessarily limit the present disclosure to any specific embodiments. Various modifications can be made to these embodiments without departing from the true scope and spirit of the present disclosure.

For example, in the embodiment described above, the casing 2 is configured such that it can be divided into the first and second cases 11 and 12. The four second cover parts 22 fill the spaces between the first cover parts 14 of the first case 11 that are adjacent to each other in the circumferential direction. According to the above-described embodiment, the micro-gap S is left between each first cover part 14 and the corresponding second cover part 22. The present disclosure, however, is not limited to such, and the second cover parts 22 may entirely block the spaces between the first cover parts 14 adjacent to each other in the circumferential direction. To be specific, the first and second cover parts 14 and 22 may be integrally molded, and the first and second cases 11 and 12 may be integrally molded. In this case, no micro-gap S is left, which can in turn prevent broken fragments (metal fragments) or the like from directly adhering to the magnet parts 4. In this manner, the abnormality detecting device 1 can stably perform accurate detection.

According to the above-described embodiment, in order to achieve as long an inter-magnet creepage distance Md as possible, the side surfaces 14a of the first cover parts 14 are overlaid on the side surfaces 22c of the second cover parts 22 in the radial direction. The present disclosure, however, is not limited to such, and any configuration is acceptable as long as the inter-electrode creepage distance Ed is less than the inter-magnet creepage distance Md. For example, a long inter-magnet creepage distance Md may be achieved by imparting a complicated shape to the side surfaces 14a and 22c of the first and second cover parts 14 and 22.

According to the above-described embodiment, the electrode parts 5 are separate from the magnet parts 4. The present disclosure, however, is not limited to such, and the electrode and magnet parts 5 and 4 may be integrally molded. For example, the electrode and magnet parts 5 and 4 may be formed by two-color molding, and only the portions corresponding to the magnet parts 4 may be magnetized. In the embodiment described above, the abnormality detecting device 1 includes four first cover parts 14, four second cover parts 22, four magnet parts 4, and four electrode parts 5. The present disclosure, however, is not limited to such, and any configuration is acceptable as long as the abnormality detecting device 1 at least includes two first cover parts 14, two second cover parts 22, two magnet parts 4, and two electrode parts 5. With such arrangement, the resistance detecting unit 41 can detect the resistance between the two electrode parts 5.

In the embodiment described above, the resistance between two of the electrode parts 5 is detected via the magnet parts 4. The detection circuit 40 is provided as a detecting unit for determining whether an abnormality occurs based on the detected resistance. When the resistance detected by the resistance detecting unit 41 reaches or falls below the specified value, the detection circuit 40 determines that the speed reducer 100 experiences abnormalities. The present disclosure, however, is not limited to such, and the detection circuit 40 may be simply configured such that it outputs a signal at the ON level (for example, light is turned on) when the resistance between the adjacent electrode parts 5 exceeds the specified value. This may indicate that the speed reducer 100 experiences abnormalities. In other words, the detected resistance may be output in various manners.

In the above-described embodiment, the metal powder particles are described as an example of the conductive particles. The present disclosure, however, is not limited to such, and the conductive particles can be any of other various conductive particles than metal powder particles. For example, other metal powder particles include particles of iron-based magnetic and conductive materials, but the abnormality detecting device 1 can also detect a conductive resin.

In the embodiment described above, the speed reducer 100 is described as an example mechanical device. The speed reducing mechanism 102 is described as an example mechanical mechanism. According to the above description, the abnormality detecting device 1 is provided in the speed reducer 100. The present disclosure, however, is not limited to such, and the abnormality detecting device 1 can be used in gear devices, or other mechanical devices including various mechanical mechanisms. The above-described embodiment includes the first and second cylindrical parts 13 and 21, which do not need to be shaped like a perfect cylinder but only need to be tubular. For example, the first and second cylindrical parts 13 and 21 may be shaped like a polygonal cylinder.

The foregoing embodiments disclosed herein describe a plurality of physically separate constituent parts. They may be combined into a single part, and any one of them may be divided into a plurality of physically separate constituent parts. Irrespective of whether or not the constituent parts are integrated, they are acceptable as long as they are configured to solve the problems.

What is claimed is:

1. An abnormality detecting device comprising:
    at least two first cover parts arranged next to each other in a circumferential direction;
    a plurality of electrode parts respectively supported by the first cover parts, each electrode part having a portion being externally exposed beyond a surface of a corresponding one of the first cover parts;
    a plurality of magnet parts provided inside of the first cover parts in a radial direction, each magnet part being in contact with a corresponding one of the electrode parts; and
    at least two second cover parts each provided between adjacent ones of the first cover parts in the circumferential direction,
    wherein at least a portion of a surface of the each electrode part that is externally exposed beyond a surface of the corresponding first cover part is oil repellent.

2. The abnormality detecting device of claim 1, wherein the first and second cover parts each have an oil-repellent surface.

3. The abnormality detecting device of claim 2,
    wherein the first and second cover parts are made of an oil-repellent resin, and
    wherein the electrode parts have an oil-repellent and conductive plating layer formed on a surface thereof.

4. The abnormality detecting device of claim 3, comprising:
    a first case having the first cover parts, the first case forming an outer shell; and a second case having the second cover parts, the second case forming the outer shell, wherein the first and second cases are made of the oil-repellent resin.

5. An abnormality detecting device comprising:
a first case having at least two first cover parts arranged next to each other in a circumferential direction, the first case forming an outer shell;
a plurality of electrode parts respectively supported by the first cover parts, each electrode part having a portion externally exposed beyond a surface of a corresponding one of the first cover parts;
a plurality of magnet parts provided inside of the first cover parts in a radial direction, each magnet part being in contact with a corresponding one of the electrode parts;
a second case having at least two second cover parts, each second cover part being provided between adjacent ones of the first cover parts in the circumferential direction, the second case forming the outer shell; and
a detecting unit for detecting a resistance between two of the electrode parts via the magnet parts to determine whether an abnormality occurs based on the detected resistance,
wherein at least a portion of a surface of the each electrode part that is externally exposed beyond a surface of the corresponding first cover part has an oil-repellent and conductive plating layer formed thereon, and
wherein the first and second cases are made of an oil-repellent resin.

* * * * *